US00PP36301P3

(12) United States Plant Patent
Rouwette

(10) Patent No.: US PP36,301 P3
(45) Date of Patent: Dec. 10, 2024

(54) ***PHYSOCARPUS* PLANT NAMED 'GRDARK01'**

(50) Latin Name: *Physocarpus opulifolius*
Varietal Denomination: GRDARK01

(71) Applicant: Guido Rouwette, Valkenburg (NL)

(72) Inventor: Guido Rouwette, Valkenburg (NL)

( * ) Notice: Subject to any disclaimer, the term of this patent is extended or adjusted under 35 U.S.C. 154(b) by 0 days.

(21) Appl. No.: 18/408,817

(22) Filed: Jan. 10, 2024

(65) Prior Publication Data

US 2024/0315154 P1 Sep. 19, 2024

(30) Foreign Application Priority Data

Mar. 13, 2023 (QZ) ..... PBR 2023/0625

(51) Int. Cl.
*A01H 6/74* (2018.01)
*A01H 5/12* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 6/74; A01H 5/12; A01H 5/02
See application file for complete search history.

*Primary Examiner* — Keith O. Robinson
(74) *Attorney, Agent, or Firm* — Cassandra Bright

(57) ABSTRACT

A new and distinct *Physocarpus* cultivar named 'GRDARK01' is disclosed, characterized by very dark purple foliage. Plants are compact, bushy and dense. The new cultivar is a *Physocarpus*, normally produced as an outdoor garden or container plant.

2 Drawing Sheets

Latin name of the genus and species: *Physocarpus opulifolius.*

Cultivar denomination: 'GRDARK01'.

BACKGROUND OF THE INVENTION

The new *Physocarpus* cultivar is a product of a planned breeding program conducted by the inventor, in Valkenburg, the Netherlands. The crossing resulting in this new cultivar was made during 2011 at a commercial nursery.

The new *Physocarpus* 'GRDARK01' resulted from the crossing of the seed parent, an unnamed, unpatented proprietary *Physocarpus opulifolius* with the pollen parent, a different unnamed, unpatented proprietary *Physocarpus opulifolius*. The new cultivar was identified as a potentially interesting selection in 2016, at the same commercial nursery in Valkenburg, the Netherlands.

Asexual reproduction of the new cultivar 'GRDARK01' by softwood cuttings was first performed during August of 2016, at the breeder's commercial greenhouse in Valkenburg, the Netherlands.

Subsequent propagation has shown that the unique features of this cultivar are stable and reproduced true to type in successive generations

SUMMARY OF THE INVENTION

The cultivar 'GRDARK01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'GRDARK01'. These characteristics in combination distinguish 'GRDARK01' as a new and distinct *Physocarpus* cultivar:

1. Very dark purple foliage, including young foliage.
2. Compact plants
3. Bushy, dense plants.

PARENT COMPARISON

Plants of the new cultivar 'GRDARK01' are similar to plants of the seed parent, in most horticultural characteristics, however, plants of the new cultivar 'GRDARK01' differ in the following:

1. 'GRDark01' produces a dark purple leaf; the seed parent produces a dark red-purple leaf.
2. 'GRDark01' produces a larger leaf by about 30% than the seed parent.

Plants of the new cultivar 'GRDARK01' are similar to plants of the pollen parent, in most horticultural characteristics, however, plants of the new cultivar 'GRDARK01' differ in the following:

1. 'GRDark01' produces a dark purple leaf; the pollen parent produces a dark red-purple leaf.

COMMERCIAL COMPARISON

Plants of the new cultivar 'GRDARK01' can also be compared to the commercial cultivar *Physocarpus opulifolius* 'Hoogi018' U.S. Plant Pat. No. 28,059. The varieties are similar in most horticultural characteristics; however 'GRDARK01' differs in the following:

1. 'GRDark01' produces a dark purple leaf; this comparator produces a leaf which is lighter in color and more greenish-black than purple-black.

Plants of the new cultivar 'GRDARK01' can also be compared to the commercial cultivar *Physocarpus opulifo-*

*lius* 'Rubella', unpatented. The varieties are similar in most horticultural characteristics; however 'GRDARK01' differs in the following:

1. 'GRDark01' produces a dark purple leaf; this comparator produces a red colored leaf.
2. Plants of 'GRDark01' are more compact than plants of 'Rubella'.

Plants of the new cultivar 'GRDARK01' can also be compared to the commercial cultivar *Physocarpus opulifolius* 'Minall2', unpatented. The varieties are similar in most horticultural characteristics; however 'GRDARK01' differs in the following:

1. 'GRDark01' produces a dark purple leaf; this comparator produces a dark red-purple colored leaf in the Spring, turning dark purple in Fall.
2. Plants of 'GRDark01' has smaller foliage than this comparator.

BRIEF DESCRIPTION OF THE PHOTOGRAPHS

The accompanying photographs illustrate in full color various distinguishing characteristic of the new cultivar, 'GRDARK01' grown outdoors in Valkenburg, the Netherlands. The photographs were taken using conventional techniques and although colors may appear different from actual colors due to light reflectance it is as accurate as possible by conventional photographic techniques.

DETAILED BOTANICAL DESCRIPTION

Figure 1:
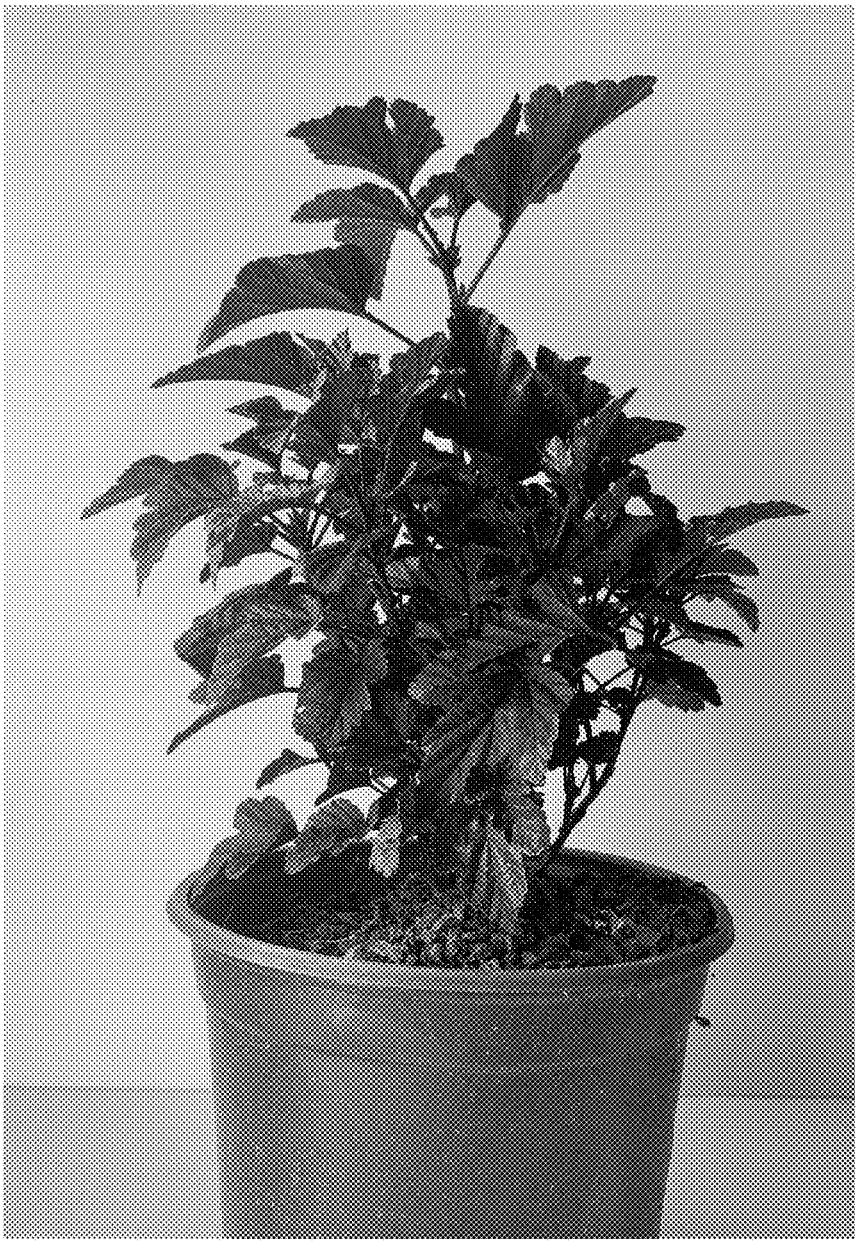
FIG. 1 illustrates a potted plant of approximately 9 months in a 3 liter pot.
Figure 2:
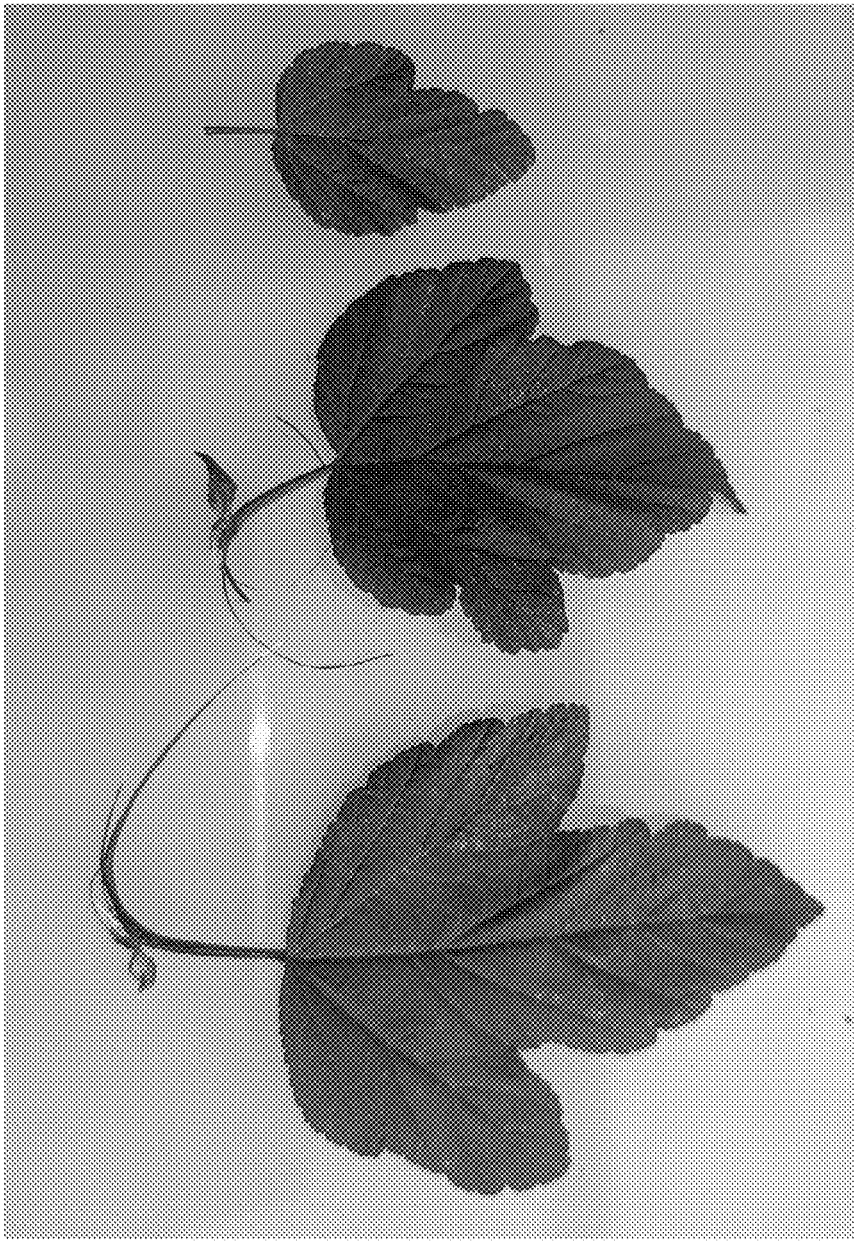
FIG. 2 illustrates a close-up view of the foliage.

In the following description, color references are made to The Royal Horticultural Society Colour Chart 2015 except where general terms of ordinary dictionary significance are used. The following observations and measurements describe 'GRDARK01' plants grown outdoors in Valkenburg, the Netherlands. The plants were approximately 3 years old grown in 19 cm containers. Measurements and numerical values represent averages of typical plant types.

Botanical classification: *Physocarpus opulifolius* 'GRDARK01'.

PROPAGATION

Time to produce a rooted cutting: About 6 to 8 weeks at approximately 20° C.

Root description: Fine, and freely branching, both fibrous and fleshy.

PLANT

Plant type: Deciduous perennial shrub.

Age of plant described: Approximately 3 years old.

Growth habit: Compact, upright and bushy.

Pot size of plant described: 19 cm pot

Height: Approximately 46 cm.

Plant spread: Approximately 32 cm.

Growth rate: Moderate.

Branching characteristics: Well-branched, freely branching from the base. 1 main stem, 5 secondary branches, 24 tertiary branches.

Length of primary lateral branches: Average 40 cm.

Diameter of lateral branches: Approximately 3 mm.

Branches:

*Appearance*.—Rounded.

*Aspect/angle*.—Most branches at acute angles, about 15°.

*Strength*.—Strong

*Texture*.—New stems: Glabrous. Oldest stems: Exfoliating bark.

*Stem color*.—New stems: Near RHS Greyed-Purple 187A and 187B. Oldest stems: Near RHS Greyed-Green 199C with exfoliating bark Brown 200B.

Internode length: Average 2.5 cm.

FOLIAGE

Leaf:

*Arrangement*.—Alternate, single.

*Average length*.—Approximately 5.2 cm.

*Average width*.—Approximately 4.8 cm.

*Shape of blade*.—Ovate. Tri-lobed

*Apex*.—Acute.

*Base*.—Cordate to obtuse.

*Attachment*.—Stalked.

*Margin*.—Crenate.

*Texture of top surface*.—Glabrous.

*Texture of bottom surface*.—Glabrous.

*Appearance of top surface*.—Glossy.

*Appearance of bottom surface*.—Matte.

*Color*.—Young foliage upper side: Near RHS Brown 200A. Young foliage under side: Near RHS Yellow-Green 148A with Greyed-Purple 187A. Mature foliage upper side: Near RHS Greyed-Purple N186A flushed Brown 200A. Mature foliage under side: Near RHS Yellow-Green 148A.

*Venation*.—Type: Palmate. Venation color upper side: Indistinguishable from leaf blade, blends in. Venation color under side: Near RHS Yellow-Green 145A.

*Petiole*.—Average Length: Approximately 1.5 cm. Diameter: Approximately 1.5 mm. Young Petiole color upper side: Near RHS Greyed-Purple 187A and 187B. Young Petiole color lower side: Near RHS Yellow-Green 145A with Greyed-Purple 187A and 187B near base of petiole. Mature Petiole color upper side: Near RHS Greyed-Purple 187A. Mature Petiole color lower side: Near RHS Yellow-Green 145A with Greyed-Purple 187A near base of petiole. Petiole Texture upper side; Glabrous. Petiole Texture lower side; Glabrous.

*Stipule*.—

*Quantity*.—2 at the base of each petiole.

*Shape*.—Narrow oblong to oblanceolate.

*Size*.—About 9 mm long and 2 mm wide.

*Color*.—Upper surface: Near Brown 200A. Lower surface: Near Yellow-Green 184A, 144C near base.

FLOWER

Not Observed to Date.

REPRODUCTIVE ORGANS

Not Observed to Date.

OTHER CHARACTERISTICS

Seeds and fruits: Not Observed to Date.

Disease/pest resistance: Neither resistance nor susceptibility to typical diseases and pests common to *Physocarpus* have been observed.

Temperature tolerance: The new cultivar tolerates temperatures between −31 to 38° C.

What is claimed is:

1. A new and distinct cultivar of *Physocarpus* plant named 'GRDARK01' as herein illustrated and described.

* * * * *